United States Patent [19]

Kirchmeyer et al.

[11] Patent Number: 5,254,660

[45] Date of Patent: Oct. 19, 1993

[54] POLYISOCYANATE SOLUTIONS USEFUL FOR IMPREGNATING POROUS INORGANIC SUBSTRATES

[75] Inventors: Stephan Kirchmeyer, Leverkusen; Hanns-Peter Müller, Odenthal-Höffe; Hermann Kober, Bergisch Gladbach; Stefan Böhm, Leverkusen; Josef Pedain, Cologne, all of Fed. Rep. of Germany

[73] Assignee: Bayer Aktiengesellschaft, Leverkusen, Fed. Rep. of Germany

[21] Appl. No.: 970,354

[22] Filed: Nov. 2, 1992

[30] Foreign Application Priority Data

Nov. 8, 1991 [DE] Fed. Rep. of Germany ....... 4136768

[51] Int. Cl.$^5$ .............................. C08G 18/32
[52] U.S. Cl. ...................... 528/49; 528/70; 427/393.6; 427/385.5; 428/307.3; 568/842; 568/843
[58] Field of Search .............. 528/49, 70; 427/393.6, 427/425.5; 428/307.3; 568/842, 843

[56] References Cited

U.S. PATENT DOCUMENTS

| | | | |
|---|---|---|---|
| 3,171,861 | 3/1965 | Ahlbrecht | 260/633 |
| 3,478,116 | 11/1969 | Smeltz | 260/633 |
| 4,046,944 | 9/1977 | Mueller et al. | 428/262 |
| 4,540,765 | 9/1985 | Koemm et al. | 528/45 |
| 4,810,536 | 3/1989 | Jansen et al | 427/421 |
| 4,826,948 | 5/1989 | Jansen et al | 528/28 |

FOREIGN PATENT DOCUMENTS

| | | |
|---|---|---|
| 127061 | 5/1984 | European Pat. Off. . |
| 283892 | 9/1988 | European Pat. Off. . |
| 405534 | 1/1991 | European Pat. Off. . |
| 435641 | 7/1991 | European Pat. Off. . |
| 1418985 | 10/1969 | Fed. Rep. of Germany . |
| 999795 | 7/1965 | United Kingdom . |

OTHER PUBLICATIONS

C. A. 69 (1968), Abstract 11 065a—JP patent application 67021 331.
M. O. in J. Fluorine Chem. 20, 313 (1981).

*Primary Examiner*—Maurice J. Welsh
*Attorney, Agent, or Firm*—Joseph C. Gil; Lyndanne M. Whalen

[57] ABSTRACT

Solutions of a) a fluorine-containing polyisocyanate in b) an isocyanate-inert solvent are used to impart water, oil and dirt resistance to porous inorganic substrates impregnated therewith. The fluorine-containing polyisocyanate is preferably selected from fluorine-containing polyisocyanates having a fluorine content in the form of perfluorinated alkyl groups of from about 15 to about 60% by weight and an isocyanate content of from about 0.5 to about 15% by weight. These isocyanates are obtained by reaction of (cyclo)aliphatic isocyanates with fluorine-containing mono- and polyhydric alcohols, and selected fluorine-containing alcohols suitable for the production of these polyisocyanates.

7 Claims, No Drawings

POLYISOCYANATE SOLUTIONS USEFUL FOR IMPREGNATING POROUS INORGANIC SUBSTRATES

BACKGROUND OF THE INVENTION

This invention relates to solutions of fluorine-containing polyisocyanates useful for impregnating porous inorganic substrates, to polyisocyanates suitable for this purpose and to alcohols suitable for the production of these polyisocyanates.

Porous inorganic substrates, such as tiles, fireclays, building bricks obtained from natural rocks, ceramics, marble, concrete, plasters, etc., undergo gradual erosion which leads to porosity, loss of binder and loss of mechanical cohesion in the inorganic material. This erosion process can be greatly accelerated by harmful environmental influences such as, for example, vehicle emissions or traces of acid in rainwater. With buildings of particular historical significance or of special interest, it is essential to keep their original appearance intact because renewal or replacement is undesirable.

It has already been proposed (DE-OS 3 629 061) to use isocyanate (NCO) prepolymers containing polysiloxane units to impregnate porous inorganic substrates. Although the recommended impregnating agents effectively hydrophobicize the treated substrates, they are still unsatisfactory in regard to oleophobicization which is equally important. That is, the polysiloxane-containing NCO prepolymers do not afford entirely satisfactory protection against the influence of aggressive organic contaminants of the type which enter the environment, for example, through the inadequate combustion of heating oils or fuels.

Polyisocyanates containing perfluoroalkyl groups are also known. For example, DE-A 0 435 641 describes polyisocyanates containing urea groups and fluorine which are recommended for impregnating ceramics or concrete or textiles. However, urea groups introduced by partial reaction of the isocyanate groups with water, adversely affect penetration into the porous mineral and, result in a poorer long-term effect. In addition, the urea groups adversely affect the water-repelling properties of the impregnated substrate.

Japanese Patent Application 67-21 331 (C.A. 69 (1968), Abstract 11 065a) describes water-repellent fluorine-containing polyisocyanates based on linear partially fluorinated alcohols and an aromatic polyisocyanate. This application does not, however, suggest that the disclosed polyisocyanates be used for impregnating porous inorganic substrates.

SUMMARY OF THE INVENTION

It is an object of the present invention to provide a new impregnating agent for porous inorganic substrates which penetrates thoroughly into the substrate and which provides a long-lasting hydrophobicizing and oleophobicizing effect.

It is another object of the present invention to provide a process for impregnating a porous inorganic substrate with a solution which will provide a long-lasting hydrophobicizing and oleophobicizing effect.

It is a further object of the present invention to provide new fluorine-containing alcohols which are useful in the production of the impregnating agent useful for porous inorganic substrates.

These and other objects which will be apparent to those skilled in the art are achieved by reacting a diisocyanate or polyisocyanate having (cyclo)aliphatically bound isocyanate groups and a molecular weight of from about 168 to about 100 with a less than equivalent amount of a fluorine-containing monohydric or dihydric alcohol. The resultant isocyanate is then put in solution in a solvent which is inert to isocyanate groups. The resultant solution is then used to impregnate porous inorganic substrates. The new fluorine-containing dihydric alcohols useful in the production of the fluorine containing isocyanates are represented by the formulae

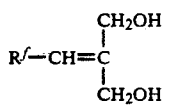

and

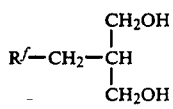

in which $R^f$ represents a perfluoroalkyl group containing from 4 to 16 carbon atoms.

DETAILED DESCRIPTION OF THE INVENTION

The present invention relates to a solution of
a) a fluorine-containing diisocyanate or polyisocyanate free from urea groups and having a fluorine content in the form of perfluorinated alkyl groups of from about 5 to about 60% by weight and an isocyanate content of 0.5 to 15% by weight in
b) a solvent inert to isocyanate groups which is useful for impregnating porous inorganic substrates.

The present invention also relates to polyisocyanates free from urea groups which are useful in the solutions of the present invention. These polyisocyanates are obtained by reacting
i) a diisocyanate or polyisocyanate containing (cyclo)aliphatically bound isocyanate groups and having a molecular weight in the range of from about 168 to about 1,000 with less than an equivalent quantity of
ii) a fluorine-containing monohydric or dihydric alcohol which is preferably selected from the group consisting of those corresponding to formulae:

 (I)

 (II)

 (III)

 (IV)

 (V)

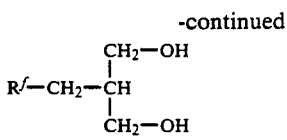

in which

R_f is a perfluoroalkyl group containing from 4 to 16 carbon atoms, $R^1$ and $R^3$ which may be the same or different each represents a $C_{1-4}$ alkyl group, $R^2$ represents a difunctional saturated aliphatic hydrocarbon radical containing from 2 to 4 carbon atoms, $R^4$ represents a trifunctional aliphatic hydrocarbon radical containing from 3 to 4 carbon atoms and n is the number 0, 1 or 2.

The resultant isocyanate reaction product may optionally be further modified. The isocyanate reaction product may also be subsequently treated to remove unreacted starting diisocyanate.

The present invention also relates to the alcohols represented by formulae (V) and (VI) which are suitable for the production of the polyisocyanates of the present invention.

The fluorine-containing diisocyanates and polyisocyanates to be used in accordance with the invention may be produced from any of the diisocyanates or polyisocyanates known to those skilled in polyurethane chemistry. Suitable diisocyanates and polyisocyanates are described, for example, by D. Dieterich in Houben-Weyl "Methoden der Organischen Chemie", Vol. E20 (Makromolekulare Stoffe), edited by H. Bartl and J. Falbe, Georg Thieme Verlag, Stuttgart/New York 1987, pages 1587 to 1595. Specific examples of appropriate isocyanates include: ethylene diisocyanate, tetramethylene diisocyanate, hexamethylene diisocyanate, 1,12-dodecane diisocyanate, cyclo-butane-1,3-diisocyanate, cyclohexane-1,3- and -1,4-diisocyanate and mixtures of these isomers, 1-isocyanato-3,3,5-trimethyl-5-isocyanato-methyl cyclohexane, 2,4- and 2,6-hexahydrotolylene diisocyanate and mixtures of these isomers, hexahydro-1,3- and/or -1,4-phenylene diisocyanates, perhydro-2,4'- and/or -4,4'-diphenylmethane diisocyanate, 1,3- and 1,4-phenylene diisocyanate, 2,4- and 2,6-tolylene diisocyanate and mixtures of these isomers, diphenylmethane-2,4'- and/or -4,4'-diisocyanate, triphenyl-methane-4,4',4''-triisocyanate, polyphenyl/-polymethylene polyisocyanates of the type obtained by phosgenation of aniline/formaldehyde condensates (See, for example, GB 874,430 and 848,671), polyisocyanates containing allophanate groups (See, for example, GB 994,890; BE 761 626; NL 7 102 524), polyisocyanates containing isocyanurate groups (See, for example, U.S. Pat. No. 3,001,973; DE-PS 1 022 789; 1 222 067; 1 027 394; DE-OS 1 929 034; 2 004 048), polyisocyanates containing urethane groups (See, for example, BE 752 261; U.S. Pat. No. 3,394,164; 3,664,457) and polyisocyanates containing biuret groups (See, for example, U.S. Pat. No. 3,124,605; 3,201,372; GB-PS 889,050).

In a preferred embodiment of the present invention, the starting polyisocyanates are those having a molecular weight in the range from 168 to 1,000 and, more particularly, in the range from 168 to 300 and containing only aliphatically and/or cycloaliphatically (hereinafter "(cyclo)aliphatically") bound isocyanate groups.

The preferred starting diisocyanates and polyisocyanates include: hexamethylene diisocyanate (HDI), 4,4'-diisocyanatodicyclohexyl methane (HMDI), 1-isocyanato -3,3,5-trimethyl-5-isocyanatomethyl cyclohexane (IPDI) and isocyanurate- and uretdione-modified derivatives of HDI and/or IPDI and bioret-modified polyisocyanates based on HDI.

The reactants for the starting diisocyanates and polyisocyanates, i.e. the fluorine-containing alcohols, are preferably those corresponding to formulae (I) to (VI) above. Those alcohols represented by formulae (I) to (IV) are compounds known from the literature. The alcohols represented by formulae (V) and (VI) are new compounds.

In each of formulae (1) through (VI), R_f represents a perfluorinated alkyl group containing from 4 to 16 and preferably from 4 to 10 carbon atoms. $R^1$, $R^2$, $R^3$, $R^4$ and n are as already defined.

Examples of suitable alcohols corresponding to formulae (I) to (IV) include: perfluoro-n-butyl ethanediol, 3-perfluor-n-butyl -1,2-propanediol, perfluoro-n-hexyl ethanediol, 3-perfluoro-n -hexyl-1,2-propanediol, 3-perfluoro-n-heptyl-1,2-propanediol, perfluorooctyl ethanediol, 3-perfluoro-n-octyl-1,2-propanediol, perfluoro-n-decyl ethanediol and 3-perfluoro-n-decyl -1,2-propanediol; compounds containing sulfonamide groups such as, for example, N-methyl-N-(2-hydroxy-ethyl)-1-perfluoro-n-butanesulfonamide, N-ethyl-N-(2-hydroxy-ethyl)-1-perfluoro -n-butanesulfonamide, N-propyl-N-(2-hydroxy-ethyl)-1-perfluoro -n-butanesulfonamide, N-methyl-N-(2,3-di-hydroxy-propyl) -1-perfluoro-n-butanesulfonamide, N,N-bis -(2-hydroxyethyl) -1-perfluoro-n-butanesulfonamide, N-methyl-N-(2-hydroxyethyl)-1-perfluoro-n-pentanesulfonamide, N-ethyl-N-(2-hydroxyethyl)-1-perfluoro-n-pentanesulfonamide, N-methyl-N-(2-hydroxyethyl)-1-perfluoro-n-hexanesulfonamide, N-ethyl-N-(2-hydroxyethyl)-1-perfluoro-n-hexanesulfonamide, N-propyl-N-(2-hydroxyethyl)-1-perfluoro-n-hexanesulfonamide, N-methyl-N-(2-hydroxyethyl)-1-perfluoro-n-heptanesulfonamide, N-ethyl-N-(2-hydroxyethyl)-1-perfluoro-n-heptanesulfonamide, N-butyl-N-(2-hydroxyethyl)-1-perfluoro-n-heptanesulfonamide, N-(2-hydroxyethyl)-1-per-fluoro-n-octanesulfonamide, N-methyl-N-(2-hydroxyethyl)-1-per-fluoro-n-octanesulfonamide, N-ethyl-N-(2-hydroxyethyl)-1-per-fluoro-n-octanesulfonamide, N-1-methylethyl-N-(2-hydroxyethyl)-1-perfluoro-n-octanesulfonamide, N-propyl-N-(2-hydroxyethyl)-1-perfluoro-n-hexanesulfonamide, N-butyl-N-(2-hydroxyethyl)-1-perfluoro-n-octane-sulfonamide, N,N-bis-(2-hydroxyethyl)-1-perfluoro-n-octane-sulfonamide, N-methyl-N-(2,3-dihydroxy-propyl)-1-perfluoro-n -octanesulfonamide, N-ethyl-N-( 2,3-di-hydroxypropyl)-1-perfluoro -n-octanesulfonamide, N-propyl-N-(2,3-dihydroxypropyl)-1-per-fluoro-n-octanesulfonamide, N-ethyl-N-(2-hydroxyethyl)-1-perfluoro-n-nonanesulfonamide, N-propyl-N-(2-hydroxyethyl)-1-perfluoro-n-decanesulfonamide and N-propyl-N-(2-hydroxyethyl)-1 -perfluoro-n -dodecanonanesulfonamide.

The new alcohols corresponding to formula (V) and (VI) may be prepared, for example, by peroxide-initiated addition of perfluoroalkyl iodides onto 3-acetoxy-2-acetoxymethyl-1-propene (VII) to form the adduct (VIII) and conversion of the adduct (VIII) by hydrogenolysis and/or hydrolysis into the alcohols (V) and (VI) in accordance with the following scheme:

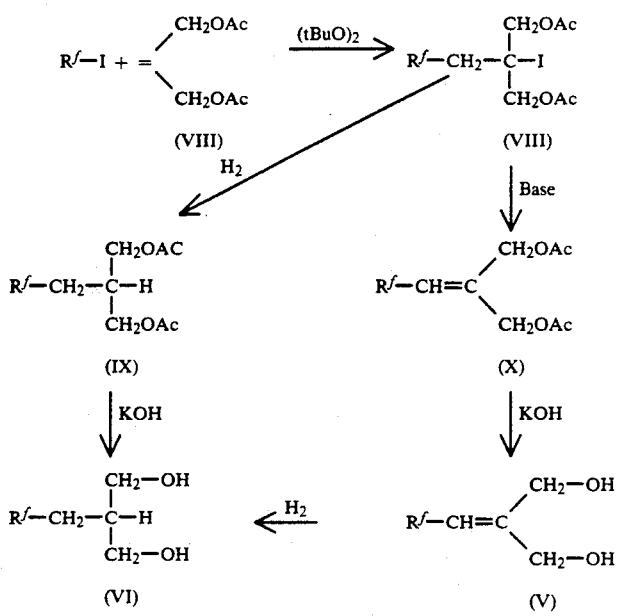

These reactions are similar to the synthesis of monofunctional alcohols containing highly fluorinated substituents by radical addition of R/I onto vinyl or allyl acetate and subsequent saponification and reductive removal of the iodine. A similar process is described, for example, in U.S. Pat. No. 3,171,861 and by M. O. Brace in J. Fluorine Chem. 20, 313 (1981).

Di-tert. butyl peroxide, for example, may be used as the initiator. The addition reaction to form the intermediate product (VIII) is generally carried out in bulk at a temperature of from 0° to 150° C. The hydrogenation reactions (formation of IX from VIII and of VI from V) may be carried out, for example, in tetrahydrofuran as the reaction medium in the presence of a known palladium catalyst at a temperature of from about 0° to about 200° C. and preferably in an inert gas atmosphere. The hydrolysis reaction (formation of VI from IX and of V from X) may be carried out in known manner. For example, hydrolysis may be carried out in aqueous methanol using alkali metal hydroxide at a temperature in the range of from 0° to 60° C.

Examples of the fluorine-containing diols (V) and (VI) which may be produced in this way include: 1,3-dihydroxy-2-(1′H,1′H-perfluoro-n-pentyl)-propane, 1,3-dihydroxy-2-(1′H,1′H-perfluoro-n-heptyl)-propane, 1,3-dihydroxy-2-(1′H,1′H-perfluoro-n-nonyl)-propane, 1,3-dihydroxy-2 -(1′H,1′H-perfluoro-n-undecyl)-propane, 3-hydroxy-2-hydroxy-methyl-1-perfluoro-n-butyl propene, 3-hydroxy-2-hydroxymethyl-1-perfluoro-n-hexyl propene, 3-hydroxy-2-hydroxymethyl-1-per-fluoro-n-octyl propene, 3-hydroxy-2-hydroxymethyl-1-perfluoro -n-decyl propene.

The fluorine-containing alcohols of formulae (I) to (IV) which are known from the literature and the new fluorine-containing alcohols (V) and (VI) of the present invention are the preferred reactants for the preparation of the fluorine-containing diisocyanates and polyisocyanates. In addition to these preferred starting materials, however, it is also possible to use other fluorine-containing alcohols such as, for example, $C_{4-20}$ alkanols containing perfluoroalkyl groups and having a fluorine content of 50 to 75% by weight or even fluorine-containing alcohols of the type described in U.S. Pat. Nos. 3,478,116; 3,504,016; 3,510,458; and 3,547,894.

The reaction between starting diisocyanate or polyisocyanate and fluorine-containing alcohol generally takes place at a temperature in the range from about 20° to about 140° C. and preferably at a temperature in the range from about 40° to about 120° C. with the equivalent ratio of isocyanate groups to hydroxyl groups being maintained at from about 6:1 to about 1.1:1 and preferably from about 3:1 to about 1.3:1 during the reaction.

The reaction is often carried out in the presence of a catalyst known to be useful for isocyanate addition reactions. Suitable catalysts include: tertiary amines, such as triethylamine, N,N-dimethyl benzylamine; monocyclic and bicyclic amidines (DE-OSI 720 633); Mannich bases; and organotin compounds, such as tin-(II) acetate, tin(II) octoate, dibutyl tin oxide and dibutyl tin dilaurate.

Where starting compounds having a functionality greater than two are used (alone or in combination with other starting components), the following equation should preferably apply:

$$f = (f_a \cdot n_a) \leq 2$$

where f is the average overall functionality of reacted isocyanate or hydroxyl groups, $f_a$ is the average isocyanate or hydroxyl functionality of the starting components involved in the reaction and $n_a$ is the molar fraction of these components based on the reaction mixture.

In general, the reaction components are stirred together at a temperature in the range of from about 20 to about 140° C. until the desired (as determined by calculation) content of excess isocyanate groups is reached.

To avoid uncontrolled reactions, the production of the urethane-containing fluorinated isocyanate may be carried out with preliminary addition of a suitable solvent or solvent mixture inert to isocyanate groups. Suitable solvents include: acetone, 2-butanone, cyclohexanone, isobutyl methyl ketone, tetrahydrofuran, methyl acetate, ethyl acetate, butyl acetate, acetonitrile, chlorobenzene, chloroform, dichloromethane, perchloroethylene, carbontetrachloride, trichloroethyl, trichloroethane, dichlorobenzenes, dimethyl formamide, 1-methyl-2-pyrrolidone, dimethyl acetamide, dimethyl sulfoxide, dioxane, hexane, heptane, isooctane, ligroin, cleaner's naphtha, soldering naphtha, light naphtha, painter's naphtha or white spirit, petroleum ether, petroleum, turpentine substitute, cyclohexane, toluene, xylene, aliphatic or aromatic painter's solvent mixtures, methyl cyclohexane, methyl glycol acetate, methoxypropyl acetate and mixtures thereof.

After the isocyanate addition, the resulting fluorine-containing diisocyanate or polyisocyanate may be subjected to a further modification and/or an after-treatment.

In the context of the invention, "further modification" is understood in particular to mean the incorporation of isocyanurate, bioret or allophanate groups. Isocyanurate groups may be incorporated, for example, by partial trimerization of the isocyanate groups still remaining after the isocyanate addition reaction in the presence of catalysts which accelerate the trimerization of isocyanate groups. A mixture of fluorine-containing diisocyanate or polyisocyanate and excess starting diisocyanate which is directly formed in the isocyanate addition reaction is generally used in this trimerization reaction. The trimerization reaction is preferably carried out using typical trimerization catalysts such as tetraalkyl ammonium hydroxides of the type described in U.S. Pat. No. 3,487,080 or DE-OS 2 839 133, at a temperature in the range from 40° to 120° C. until the desired degree of trimerization is reached. The trimerization reaction is terminated in known manner by addition of a catalyst poison and/or by thermal decomposition of the catalyst.

Instead of a starting mixture of fluorine-containing diisocyanate or polyisocyanate and excess starting diisocyanate or polyisocyanate, mixtures of fluorine-containing polyisocyanates of the present invention and other known diisocyanates of the type mentioned by way of example above and, optionally, excess starting diisocyanate or polyisocyanate of the type used in the production of the fluorine-containing diisocyanates or polyisocyanates may also be used in the trimerization reaction.

The biuretization reaction is carried out using the same starting mixtures which may be used for trimerization, although the reaction is carried out in the presence of known "biuretizing agents". Suitable biuretizing agents include t-butanol and water which are added to the mixture in a quantity of approx. 4 to 15 mol%, based on the isocyanate groups of the starting mixture. The biuretization reaction is typically carried out by heating the mixture to approx. 100° to 180° C. until the clouding which is indicative of the presence of urea groups has completely disappeared.

The allophanatization reaction may be carried out, for example, by heating a starting mixture of the type described above as being suitable for the trimerization reaction to a temperature of 60° to 120° C., optionally in the presence of a catalyst. Examples of suitable catalysts include: benzyl trimethyl ammonium hydroxide and hydroxyethyl trimethyl ammonium hydroxide, which simultaneously catalyze partial trimerization; and acids such as, for example, HCl, which result in the formation of pure allophanate products.

The heat is removed on reaching the desired degree of allophanatization which may be determined from the isocyanate content.

After their production or after any of the modification reactions described, the fluorine-containing diisocyanate or polyisocyanate obtained by reaction of the starting diisocyanate or polyisocyanate with the fluorine-containing alcohols may be freed from any starting diisocyanate or polyisocyanate still present by any of the known techniques, such as thin-layer evaporation.

The diisocyanates and polyisocyanates of the present invention based on the fluorine-containing alcohols (1) to (VI), have an isocyanate content of 0.5 to 15% by weight, preferably 4 to 12% by weight, a molecular weight $M_n$ of 600 to 4,000, preferably 1,500 to 2,500, a fluorine content in the form of perfluorinated alkyl groups of 15 to 60%, preferably 20 to 40% and a content of free excess starting polyisocyanate of preferably less than 10 and, more preferably, less than 6% by weight.

The fluorine-containing diisocyanates and polyisocyanates of the present invention are generally used in the form of a 1 to 30% by weight, preferably 1 to 10% by weight solution in at least one solvent which is inert towards isocyanate groups as impregnating agents for porous inorganic substrates. The substrates impregnated with these solutions are water-, oil- and dirt-repellent. Suitable porous inorganic substrates include ceramics, concrete and natural stone. The impregnating agent is applied by known methods such as flood coating, spray coating, roll coating, dip coating and brush coating.

Having thus described our invention, the following Examples are given as being illustrative thereof. In these Examples, all percentages are percentages by weight.

EXAMPLES

Examples 1–3

Preparation of diols of formulae (V) and (VI)

Example 1

Preparation of 1,3-Dihydroxy-2-(1'H,1'H-perfluoro-n-heptyl)-propane (VI)

1.1 1,3-Diacetoxy-2-iodo-2-(1'H,1'H-perfluoro-n-heptyl)-propane (VIII)

25 g (0.17 mol) of ditertiary butyl peroxide and 115 g (0.66 mol) of 3-acetoxy-2-acetoxymethyl-2-propene (VII) were added to 1.5 kg (3.36 mol) of perfluoro-n-hexyl iodide. The mixture was then heated under nitrogen to 115°–120° C. Another 115 g (0.66 mol) of 3-acetoxy-2-acetoxymethyl-1-propene (VII) were then added dropwise with stirring at 115°–120° C., followed by stirring for 8 h at 120° C. (until all the 3-acetoxy-2-acetoxymethyl-1-propene had reacted). The excess perfluorohexyl iodide was then distilled off. 750 g of the product 1,3-diacetoxy-2-iodo-(1'H,1'H-perfluoro-n-heptyl) -propane (i.e., 91% of the theoretical yield) were obtained in the form of a crystalline solid.

1.2
1,3-Diacetoxy-2-(1'H,1'H-perfluoro-n-heptyl)-propane (IX)

507 g (0.82 mol) of the 1,3-diacetoxy-2-iodo-2-(1'H,1'H-perfluoro-n-heptyl)-propane (VIII) were dissolved in 3,000 ml tetrahydrofuran (THF) and 91 g (0.9 mol) of triethylamine were added to the resulting solution. 20 g Pd/C (10%) were then added and the mixture was hydrogenated for 5 hours at 35° C. The palladium catalyst was then filtered off and the solvent was distilled off. The residue was taken up in dichloromethane and washed with water, 5% NaHSO₃ solution and again with water. After drying with MgSO₄, the mixture was concentrated in a rotary evaporator and the residue was distilled in a high vacuum. Bp.$_{1.3\ mbar}$: 102° C. Yield: 152 g (38%).

1.3 1,3-Dihydroxy-2-(1'H,1'H-perfluoro-n-heptyl)-propane (VI)

150 g (0.3 mol) of 1,3-diacetoxy-2-(1'H,1'H-perfluoro-heptyl)-propane (IX) were added to a solution of 84 g (1.45 mol) of KOH in 600 ml methanol, followed by stirring for 16 h at room temperature. 2 l of water were then added and the mixture was thoroughly extracted with methyl-tert-butyl ether (MTBE). The combined organic phases were washed with water, dried with MgSO₄ and concentrated in a rotary evaporator. The residue was distilled in a high vacuum. Bp.$_{0.05\ mbar}$: 110° to 111° C. Yield: 89 g (72%). Mp.: 74° to 76° C.

Example 2

Preparation of
3-Hydroxy-2-hydroxymethyl-1-perfluoro-n -hexyl propene (V)

2.1 3-Acetoxy-2-acetoxymethyl-1-perfluoro-n-hexyl propene (X)

2.17 kg (3.5 mol) of 1,3-diacetoxy-2-iodo-2-(1'H,1'H-perfluoro-n-heptyl)-propane (VIII) were dissolved in 2.5 l dichloromethane and 485 g (3.9 mol) of DBN*) were added dropwise with stirring to the resulting solution at 0° C. The mixture was then stirred at 0° C. until the conversion was complete as determined by gas chromatography (GC) (approx. 15 h). The reaction mixture was then washed with 10% NH₄Cl solution, 5% NaHSO₃ solution and water. After drying with MgSO₄, the solvent was distilled off. Yield: 1.79 kg (94% of the theoretical).
*) 1,5-diazabicyclo 4.3.0non-5-ene 2.2 3-Hydroxy-2-hydroxymethyl-1-perfluoro-n-hexyl propene (V)

1.345 kg (2.74 mol) of 3-acetoxy-2-acetoxymethyl-1-perfluoro-n-hexyl propene (X) were dissolved in 1.5 l methanol. A solution of 150 g (2.7 mol) KOH in 400 ml methanol was added to the resulting solution. The reaction mixture was then stirred overnight at room temperature. 2 l of saturated NH₄Cl solution were then added to the mixture, the phases were separated and the aqueous phase was extracted with MTBE. The combined organic phases were dried with MgSO₄, concentrated and distilled in a high vacuum.

Bp.$_{0.03\ mbar}$: 105° to 110° C. Yield: 725 g (66%).

Example 3

Preparation of 1,3-Dihydroxy-2-(1'H,1'H-perfluoro-n -heptyl)-propane (VI)

1.5 kg (3.7 mol) of 3-hydroxy-2-hydroxymethyl-1-perfluoro-n -hexyl propene (V) were dissolved in 4 l THF and 375 g Raney nickel were added to the resulting solution in an autoclave. Hydrogen was then introduced to a pressure of 140 bar and the reaction mixture was hydrogenated for a total of 70 hours at 120° to 130° C. After cooling and venting, the catalyst was filtered off. The solution was concentrated and subjected to fractional distillation in vacuo.

1st Fraction:
Secondary product:
1-hydroxy-2-(1'H,1'H-perfluoroheptyl)-propane
Bp.$_{12\ mbar}$: 88° C.
Yield: 198 g (14%).
2nd Fraction:
1,3-Dihydroxy-2-(1'H,1'H-perfluoroheptyl)-propane (VI)
Bp.$_{0.05\ mbar}$: 110°–111° C.
Mp.: 74° to 76° C.
Yield: 1,105 g (73%)

Examples 4–6

Preparation of polyisocyanates according to the invention

Example 4

19.76 g (0.04 mol) of 1-perfluoro-n-octyl-2,3-dihydroxypropane and 6.66 g (0.06 mol) of isophorone diisocyanate were combined in the absence of moisture in a mechanically stirred 100 ml three-necked flask equipped with an internal thermometer. This mixture was stirred at 120° C. until the product had an isocyanate content of 3.0% (as determined by titration). The product was dissolved in 26.42 g of butyl acetate, giving a clear 50% solution of a fluorine-containing polyisocyanate which, based on solids, had a fluorine content of 57.8% and an NCO content of 3.0%.

Example 5

15.48 g (0.04 mol) of bis-(2-hydroxyethyl)-1-perfluoro-n-butanesulfonamide and 6.66 g (0.06 mol) of isophorone diisocyanate were combined in the absence of moisture in a mechanically stirred 100 ml three-necked flask equipped with an internal thermometer. This mixture was stirred at 120° C. until the product had an isocyanate content of 4.0% (as determined by titration). The product was dissolved in 22.14 g of butyl acetate, giving a clear 50% solution of a polyisocyanate which, based on solids, had a fluorine content of 30.9% and an NCO content of 4.0%.

Example 6

49.1 g of an isocyanurate polyisocyanate based on HDI with an NCO content of 21.4% and 44.6 g of N-methyl-N-(2-hydroxy-ethyl)-1 -perfluoro-n-butanesulfonamide were combined in the absence of moisture in a mechanically stirred 250 ml three-necked flask equipped with an internal thermometer. This mixture was stirred at 100° C. until the product had an isocyanate content of 5.6% (as determined by titration). The product was dissolved in 93.7 g of methoxypropyl acetate to give a clear solution of a fluorine-containing polyisocyanate which, based on solids, had a fluorine content of 22.8% and an NCO content of 5.6%.

Example 7

45.6 g of a bioret polyisocyanate based on HDI with an NCO content of 23.0% and 44.6 g of N-methyl-N-(2-hydroxyethyl)-1 -perfluoro-n-butanesulfonamide were combined in the absence of moisture in a mechanically stirred 250 ml three-necked flask equipped with an internal thermometer. This mixture was stirred at 100° C. until the product had an isocyanate content of 5.7% (as determined by titration). The product was dissolved in 93.7 g methoxypropyl acetate, giving a clear, slightly yellowish 50% solution of a fluorine-containing polyisocyanate which, based on solids, had a fluorine content of 23.7% and an NCO content of 5.7%.

Example 8

49.1 g of the isocyanurate polyisocyanate of Example 6 and 35.7 g of N-methyl-N-(2-hydroxyethyl)-1-perfluoro-n-butanesulfonamide were combined in the absence of moisture in a mechanically stirred 250 ml three-necked flask equipped with an internal thermometer. This mixture was stirred at 100° C. until the product had an isocyanate content of 7.5% (as determined by titration). The product was dissolved in 198 g of butyl acetate, giving a clear 30% solution of a fluorine-containing polyisocyanate which, based on solids, had a fluorine content of 20.2% and an NCO content of 7.5%.

Example 9

49.1 g of the isocyanurate polyisocyanate of Example 6 and 53.6 g of N-methyl-N-(2-hydroxyethyl)-1-perfluoro-n-butanesulfonamide were combined in the absence of moisture in a mechanically stirred 250 ml three-necked flask equipped with an internal thermometer. This mixture was stirred at 100° C. until the product had an isocyanate content of 4.3% (as determined by titration). The product was dissolved in 240 g butyl acetate, giving a clear 30% solution of a fluorine-containing polyisocyanate which, based on solids, had a fluorine content of 25.0% and an NCO content of 4.3%.

Example 10

49.1 g of the isocyanurate polyisocyanate of Example 6 and 62.48 g of N-methyl-N-(2-hydroxyethyl)-1-perfluoro-n-butanesulfonamide were combined in the absence of moisture in a mechanically stirred 250 ml three-necked flask equipped with an internal thermometer. This mixture was stirred at 100° C. until the product had an isocyanate content of 2.8% (as determined by titration). The product was dissolved in 260 g butyl acetate, giving a clear 30% solution of a fluorine-containing polyisocyanate which, based on solids, had a fluorine content of 26.0% and an NCO content of 2.8%.

Example 11

40.8 g (0.1 mol) of compound (VI) from Example I and 33.3 g (0.2 mol) of isophorone diisocyanate were stirred for 5 h at 100° C. in the absence of moisture. The highly viscous prepolymer was dissolved in butyl acetate to form a 30% solution. The clear solution had an isocyanate content of 1.66% (as determined by titration).

Example 12 (use)

Solutions of each of the polyisocyanates of Example 4 to 10 were adjusted to a solids content of 10% by weight by addition of the solvent used in the particular Example. Ceramic tiles measuring 5.0×7.0×0.5 cm were then immersed in these solutions for 30 seconds and conditioned for 7 days at room temperature (23° C.) and for 24 hours at 50° C. Water absorption was determined by storage under water for 24 hours (depth approx. 1 to 2 mm). The results are set out in Table 1.

TABLE 1

| Impregnation with solution of isocyanate from | Fluorine content in solid | Average application of impregnation | Water absorption after 24 h | Hydrophobicizing effect **) |
|---|---|---|---|---|
| Example 4 | 57.8% | 46.0 g/m² | 0.1% | 99.5% |
| Example 5 | 30.9% | 40.4 g/m² | 0.55% | 97.4% |
| Example 6 | 22.8% | 30.4 g/m² | 0.34% | 98.4% |
| Example 7 | 23.7% | 26.9 g/m² | 0.36% | 98.3% |
| Example 8 | 20.2% | 29.1 g/m² | 0.40% | 98.1% |
| Example 9 | 25.0% | 28.6 g/m² | 0.46% | 97.9% |
| Example 10 | 26.0% | 33.9 g/m² | 0.52% | 97.6% |
| Example 11 | 33.3% | 80.8 g/m² | 0.43% | 98.0% |
| Comp. *) | None | 35.1 g/m² | 6.13% | 71.5% |
| Comp. (untreated ceramic) | None | 0 g/m² | 21.5% | 0% |

*) Impregnation with a commercially available 35% aqueous siloxane dispersion (Baysilone LD) diluted with water to 5% solids

**) Hydrophobicizing effect: $\left(1 - \dfrac{\text{Water absorption Example}}{\text{water absorption untreated ceramic}}\right) \times 100$

Examples 13–16

(Preparation of polyisocyanates useable in accordance with the invention)

Example 13

This Example describes the preparation of a diisocyanate containing urethane groups from hexamethylene diisocyanate (HDI) and the compound represented by formula V which was prepared by the procedure described in Example 2.2.

40.8 g of the compound represented by formula V prepared in accordance with Example 2.2 were introduced into 101 g of HDI with thorough stirring and heating to 100° C., followed by heating for 2 hours at 100° C. Excess HDI was distilled off in a thin-layer evaporator at 140° C. 71 g of a substantially difunctional isocyanate in the form of a viscous clear liquid were obtained as the non-distillable residue.

Example 14

This Example describes the production of a polyisocyanate containing urethane and isocyanate groups from hexamethylene diisocyanate (HDI) and the compound represented by formula V of Example 2.2.

840 g HDI were heated to 65° C. and 7.5 g of a solution of benzyl trimethyl ammonium hydroxide in 2-ethylhexane-1,3-diol (0.5%) were added dropwise. A slightly exothermic reaction began and the temperature rose to 70° C. After about 5 hours, the trimerization reaction was terminated by addition of 0.075 g of a short-stopping solution (dibutyl phosphate, 25% in HDI). 204 g of the compound represented by formula V from Example 2.2 were then added, followed by heating for another 2 hours at 100° C. The clear reaction mixture was subjected to thin-layer distillation to remove free HDI. The product obtained was a clear liquid having a viscosity of 4400 mpa:s/ 23° C., an NCO content of 13.4% and a fluorine content of 25.3%.

Example 15

A polyisocyanate containing isocyanurate and urethane groups was prepared as in Example 14 from 840 g of HDI and 161 g of the compound

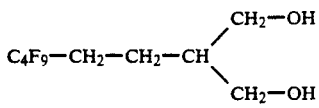

After excess HDI had been distilled off, 527 g of a viscous liquid having the following characteristics were obtained: NCO: 14.9%. Fluorine content: 16.2%. Viscosity: 7,000 mPas/23° C.

Example 16

A polyisocyanate containing isocyanurate and urethane groups was prepared as in Example 14 from 840 g of HDI and 204 g of the compound represented by formula VI prepared in accordance with Example 1.3. After the removal of excess HDI, 540 g of a viscous liquid having the following characteristic data were obtained: NCO: 14.0%. Fluorine content: 22.9%. Viscosity: 7,450 mPas/23° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A fluorine-containing diisocyanate or polyisocyanate having a fluroine content determined as perfluorinated alkyl group content of from 15 to about 60% by weight, an isocyanate content of from about 0.5 to about 15% by weight and urethane groups which is the reaction product of
   a) a diisocyanate or polyisocyanate having (cyclo)aliphatically bound isocyanate groups and a molecular weight of from about 168 to about 1,000 and
   b) a less than equivalent amount of a fluroine-containing monohydric or dihydric alcohol selected from the group consisting of

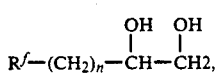 (I)

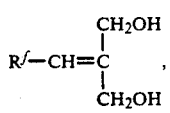 (II)

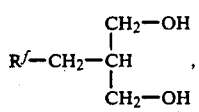 (III)

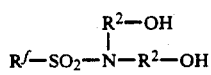 (IV)

and

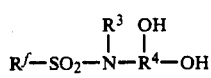 (V)

in which
R$^f$ represents a perfluoroalkyl group containing from 4 to 26 carbon atoms, and
R$^2$ represents a difunctional saturated aliphatic hydrocarbon radical containing from 2 to 4 carbon atoms, R$^3$ represents a C$_1$–C$_4$ alkyl group,
R$^4$ represents a trifunctional saturated aliphatic hydrocarbon radical containing from 3 to 4 carbon atoms, and
n represents 0, 1 or 2.

2. The diisocyanate or polyisocyanate of claim 1 in which any unreacted diisocyanate or polyisocyanate starting material is removed.

3. A process for treating a porous inorganic substrate to impart water, oil and dirt repellant protection to that substrate comprising impregnating the porous inorganic substrate with a solution of
   a) a fluorine-containing diisocyanate or polyisocyanate having from about 15 to about 60% by weight perfluorinated alkyl groups present and an isocyanate content of from about 0.5 to about 15% by weight which is the reaction product of
      1) a diisocyanate or polyisocyanate having a molecular weight in the range of from about 168 to about 1,000 and isocyanate groups which are (cyclo)aliphatically bound
      (2) less than an equivalent quantity of a fluorine-containing alcohol selected from the group consisting of

 (I)

 (II)

 (III)

 (IV)

and

 (V)

in which
R$^f$ represent a perfluoroalkyl group having from 4 to 16 carbon atoms
R$^2$ represent a difunctional saturated aliphatic hydrocarbon radical containing from 2 to 4 carbon atoms.
R$^3$ represents a C$_1$–C$_4$ alkyl group,
R$^4$ represents a trifunctional saturated aliphatic hydrocarbon radical containing from 3 to 4 carbon atoms, and
n represents 0, 1 or 2
   b) a solvent which does not react with the isocyanate groups.

4. The process of claim 3 in which the fluroine-containing diisocyanate or polyisocyanate contains urethane groups and is substantially free of urea groups.

5. The process of claim 3 in which any unreacted diisocyanate or polyisocyanate starting material is removed from the fluroine-containing diisocyanate or polyisocyanate.

6. An inorganic substrate coated with a solution of a fluorine-containing diisocyanate or polyisocyanate produced by the process of claim 3.
7. A fluroine-containing dihydric alcohol represented by the formula
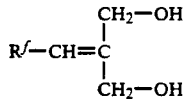
or
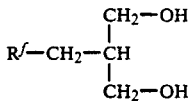
in which
R$^f$ represents a perfluoroalkyl group containing from 4 to 16 carbon atoms.
* * * * *

UNITED STATES PATENT AND TRADEMARK OFFICE
CERTIFICATE OF CORRECTION

PATENT NO. : 5,254,660  
DATED : October 19, 1993  
INVENTOR(S) : Stephan Kirchmeyer et al Page 1 of 2

It is certified that error appears in the above-indentified patent and that said Letters Patent is hereby corrected as shown below:

At column 2, line 34, delete "5 to about 60% by weight" and insert --15 to about 60% by weight--.

At column 4, lines 6-7, delete "bioret-modified" and insert --biuret-modified--.

At column 4, line 22, delete "3-perfluor-n-butyl" and insert --3-perfluoro-n-butyl--.

At column 6, line 40, delete "(DE-OSI 720 633)" and insert --(DE1 720 633)--.

At column 7, line 19, delete "bioret" and insert --biuret--.

At column 10, line 59, delete "bioret" and insert --biuret--.

At column 11, line 45, delete "Example I" and insert --Example 1--.

In Claim 1, at column 13, line 65, delete "4 to 26 carbon atoms" and insert --4 to 16 carbon atoms--.

UNITED STATES PATENT AND TRADEMARK OFFICE
CERTIFICATE OF CORRECTION

PATENT NO. : 5,254,660           Page 2 of 2
DATED      : October 19, 1993
INVENTOR(S): Stephan Kirchmeyer et al It is certified that error appears in the above-indentified patent and that said Letters Patent is hereby corrected as shown below:

In Claim 3, at column 14, line 32, delete the formula and insert

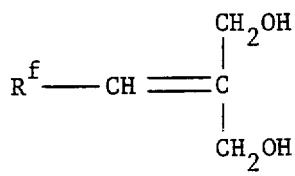

Signed and Sealed this

Thirty-first Day of October 1995

Attest:

BRUCE LEHMAN

Attesting Officer        Commissioner of Patents and Trademarks